(12) United States Patent
Millett et al.

(10) Patent No.: US 10,925,688 B2
(45) Date of Patent: Feb. 23, 2021

(54) AUXILIARY SMALL VASCULATURE GUIDEWIRE

(71) Applicant: Volcano Corporation, San Diego, CA (US)

(72) Inventors: Bret Millett, Folsom, CA (US); Joseph Burnett, Carlsbad, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 43 days.

(21) Appl. No.: 15/466,783

(22) Filed: Mar. 22, 2017

(65) Prior Publication Data

US 2018/0272111 A1 Sep. 27, 2018

Related U.S. Application Data

(63) Continuation of application No. 14/210,872, filed on Mar. 14, 2014, now abandoned.

(60) Provisional application No. 61/783,023, filed on Mar. 14, 2013.

(51) Int. Cl.
| | | |
|---|---|---|
| *A61M 25/09* | (2006.01) | |
| *A61M 25/01* | (2006.01) | |
| *A61B 90/00* | (2016.01) | |
| *A61M 25/10* | (2013.01) | |

(52) U.S. Cl.
CPC ....... *A61B 90/37* (2016.02); *A61M 25/09041* (2013.01); *A61B 2090/376* (2016.02); *A61M 2025/0177* (2013.01); *A61M 2025/1045* (2013.01)

(58) Field of Classification Search
CPC ... A61M 25/09; A61M 25/0158; A61B 90/37; A61B 2090/376
USPC .................................................. 604/500–522
See application file for complete search history.

(56) References Cited

U.S. PATENT DOCUMENTS

| | | | |
|---|---|---|---|
| 7,695,491 B2* | 4/2010 | Clubb | A61F 2/013 606/200 |
| 9,278,198 B2* | 3/2016 | Wood | A61M 25/0023 |
| 2001/0049548 A1 | 12/2001 | Vardi | |
| 2002/0183763 A1 | 12/2002 | Callol | |
| 2006/0100694 A1 | 5/2006 | Globerman | |
| 2006/0293695 A1* | 12/2006 | Ricci | A61F 2/954 606/108 |
| 2007/0010763 A1 | 1/2007 | Lentz et al. | |

(Continued)

FOREIGN PATENT DOCUMENTS

| | | |
|---|---|---|
| WO | 2007057132 A1 | 5/2007 |
| WO | 2009046097 A1 | 4/2009 |

*Primary Examiner* — Phillip A Gray

(57) ABSTRACT

The invention generally relates to an auxiliary guidewire for an intravascular procedure. The invention provides an auxiliary guidewire that slips over a primary guidewire and can provide a very fine extension beyond the end of the primary guidewire. The primary guidewire can be taken to its limit within the fine vasculature, and the auxiliary guidewire can then extend further into the fine vasculature. The primary guidewire can be taken to a bifurcation. The primary guidewire and the auxiliary guidewire can be sent down separate branches of the bifurcation. A physician can select which of the primary guidewire and the auxiliary guidewire are within the branch that needs to be treated by, for example, consulting an angiography display.

20 Claims, 6 Drawing Sheets

(56) References Cited

U.S. PATENT DOCUMENTS

| | | |
|---|---|---|
| 2007/0112331 A1 | 5/2007 | Weber |
| 2007/0167065 A1 | 7/2007 | Melsheimer et al. |
| 2007/0184707 A1 | 8/2007 | Melsheimer |
| 2007/0208276 A1 | 9/2007 | Volk |
| 2008/0109061 A1* | 5/2008 | Gregorich ......... A61M 25/1027 623/1.12 |
| 2010/0056985 A1 | 3/2010 | Weber |
| 2010/0292614 A1 | 11/2010 | Delaney |

* cited by examiner

AUXILIARY SMALL VASCULATURE GUIDEWIRE

CROSS-REFERENCE TO RELATED APPLICATION

This application is a divisional application of U.S. patent application Ser. No. 14/210,872, filed Mar. 14, 2014, which claims the benefit of, and priority to, U.S. Provisional Patent Application No. 61/783,023, filed Mar. 14, 2013, which is incorporated by reference.

FIELD OF THE INVENTION

The invention generally relates to auxiliary guidewires for intravascular procedures that operate with guidewires for intravascular procedures.

BACKGROUND

Some people are at risk of having a heart attack or stroke due to fatty plaque buildups in their arteries that restrict the flow of blood or even break off and block the flow of blood completely. Angioplasty is a procedure for treating sites that are affected by plaque. In this procedure, a needle is used to make an opening through a patient's skin. A guidewire is then inserted through the hole and guided through an artery and to the affected site. The physician tries to guide the wire by twisting and manipulating the proximal end that sits outside the patient.

The guidewire is meant to help in a number of treatment options. For example, an imaging guidewire (e.g., with an ultrasound or optical imaging sensor) can be used to visualize the affected site. If the affected blood vessel is severely narrowed by plaque buildup, the guidewire can be used to deliver, via a catheter, a balloon or stent to the affected site in hopes of opening up the narrowed vessel. If the affected site is totally occluded, the guidewire or a specialized tool can be used to cut through the occlusion.

A number of problems are associated with these procedures. For example, blockage may occur in vasculature that is too fine for a standard guidewire. A guidewire fine enough to reach such vessels may be too floppy to use. Branched vessels also present navigational challenges. It can be difficult to guide a wire into the correct branch.

SUMMARY

The invention provides an auxiliary guidewire that slips over a primary guidewire and can provide a very fine extension beyond the end of the primary guidewire. The primary guidewire can be taken to its limit within the fine vasculature, and the auxiliary guidewire can then extend further into the fine vasculature. The primary guidewire can be taken to a bifurcation. The primary guidewire and the auxiliary guidewire can be sent down separate branches of the bifurcation. A physician can select which of the primary guidewire and the auxiliary guidewire are within the branch that needs to be treated by, for example, consulting an angiography display. The other guidewire can be removed, and the treatment can be delivered by catheter to the correct branch of the bifurcation. An auxiliary guidewire slips over the primary guidewire by means of a sleeve member. In some embodiments, the sleeve member can be loosened or contracted by, for example, including an electroactive polymer in the sleeve member. This allows the auxiliary guidewire to alternatively be moved along with, or moved along relative to, the primary guidewire. Using an auxiliary guidewire as a very fine extension of a primary guidewire thus gives a physician tools for navigating the very fine vasculature of a patient. Fatty plaque buildups that otherwise could not be treated can be treated.

In certain aspects, the invention provides an auxiliary guidewire comprising at least one sleeve member disposed along an extended body. The sleeve member preferably defines an aperture area of about 0.014". The auxiliary guidewire preferably is a sub-0.014" auxiliary guidewire. The sleeve member may include at least one section of electroactive polymer. The auxiliary guidewire may include a plurality of sleeve members. A sleeve member may include a skive.

Aspects of the invention provide a system for treating the fine vasculature, the system including a guidewire, a catheter, and an auxiliary guidewire. The guidewire is preferably a standard 0.014" guidewire. And the auxiliary guidewire includes at least one sleeve member disposed along an extended body having an aperture area of about 0.014". The auxiliary guidewire preferably is a sub-0.014" auxiliary guidewire. The sleeve member may include at least one section of electroactive polymer.

In related aspects, the invention provides a method of inserting a catheter into a selected branch of a bifurcation. The method includes viewing the bifurcation on an angiographic display. A select branch of the bifurcation is identified for treatment. A guidewire is inserted up to the bifurcation. An auxiliary guidewire is slid over the guidewire and brought to the branch. The auxiliary guidewire is sent down one branch and the guidewire is sent down the other branch. Which of the auxiliary guidewire and the guidewire is within the select branch is identified by the angiographic display. The other of the auxiliary guidewire and the guidewire is removed. A catheter is delivered to the select branch.

DETAILED DESCRIPTION

The invention provides an auxiliary guidewire for an intravascular procedure that includes one or more sleeve or skive (e.g., made with an electroactive polymer) at one or a number of locations along the auxiliary guidewire. Preferably, the auxiliary guidewire is a sub-0.014" guidewire and can be inserted onto and slid along a standard (e.g., 0.014") guidewire. The guidewire, the auxiliary guidewire, or both can be used in an intravascular procedure, such as crossing a chronic total occlusion or delivering a balloon or stent in a coronary angioplasty procedure.

Figures 1, 2:
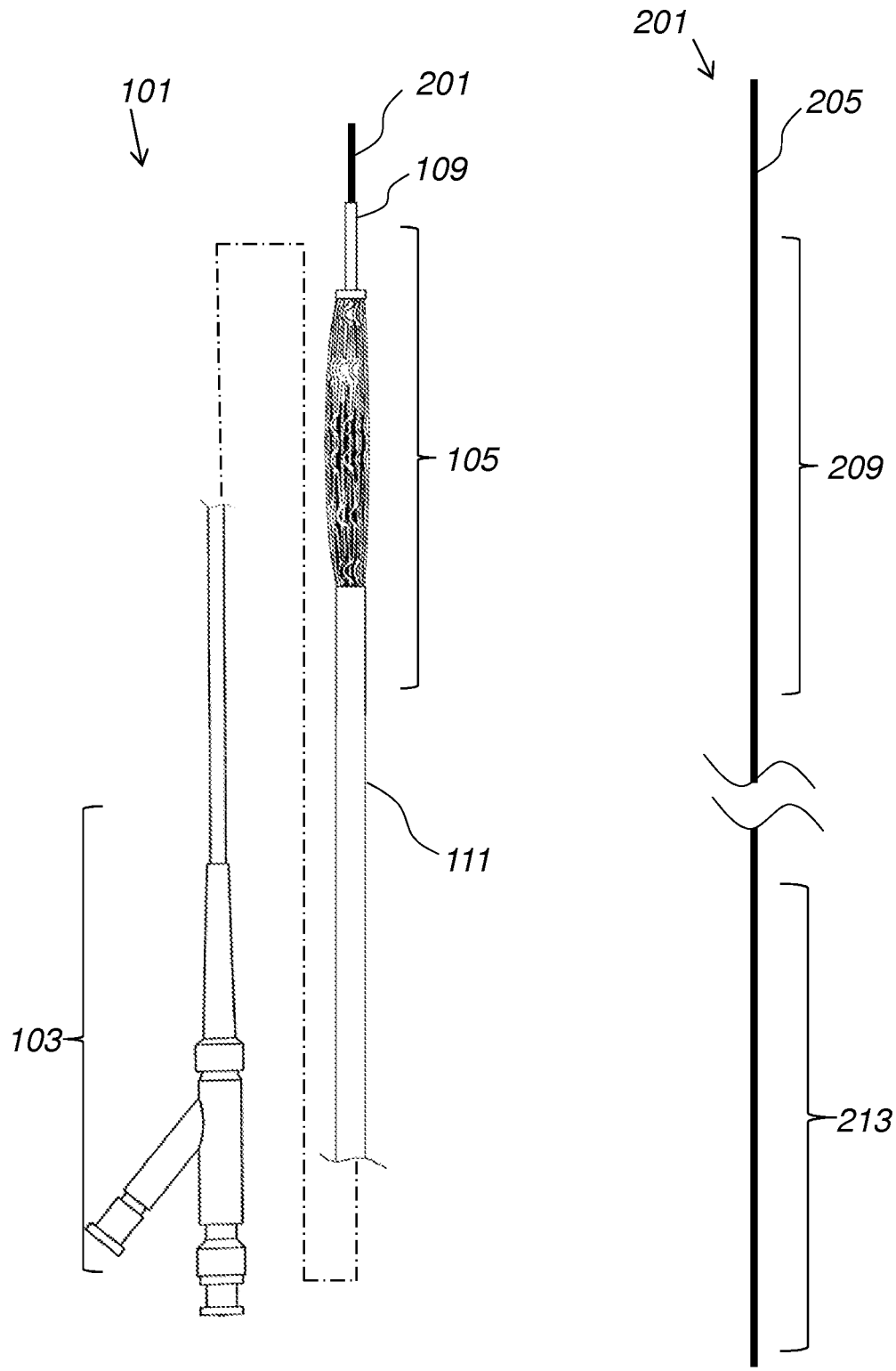
FIG. 1 shows a catheter with a guidewire.
FIG. 2 shows a guidewire.

FIG. 1 shows a catheter 101 with a guidewire 201 disposed therethrough. Catheter 101 generally includes a proximal portion 103 extending to a distal portion 111.

Optionally, a therapeutic device 105, such as a balloon or stent, may be located near distal tip 109.

FIG. 2 shows guidewire 201 including a proximal portion 213 extending to a distal portion 209 and terminating at distal tip 205. Guidewire 201 is preferably a standard 0.014" guidewire.

Figure 3:
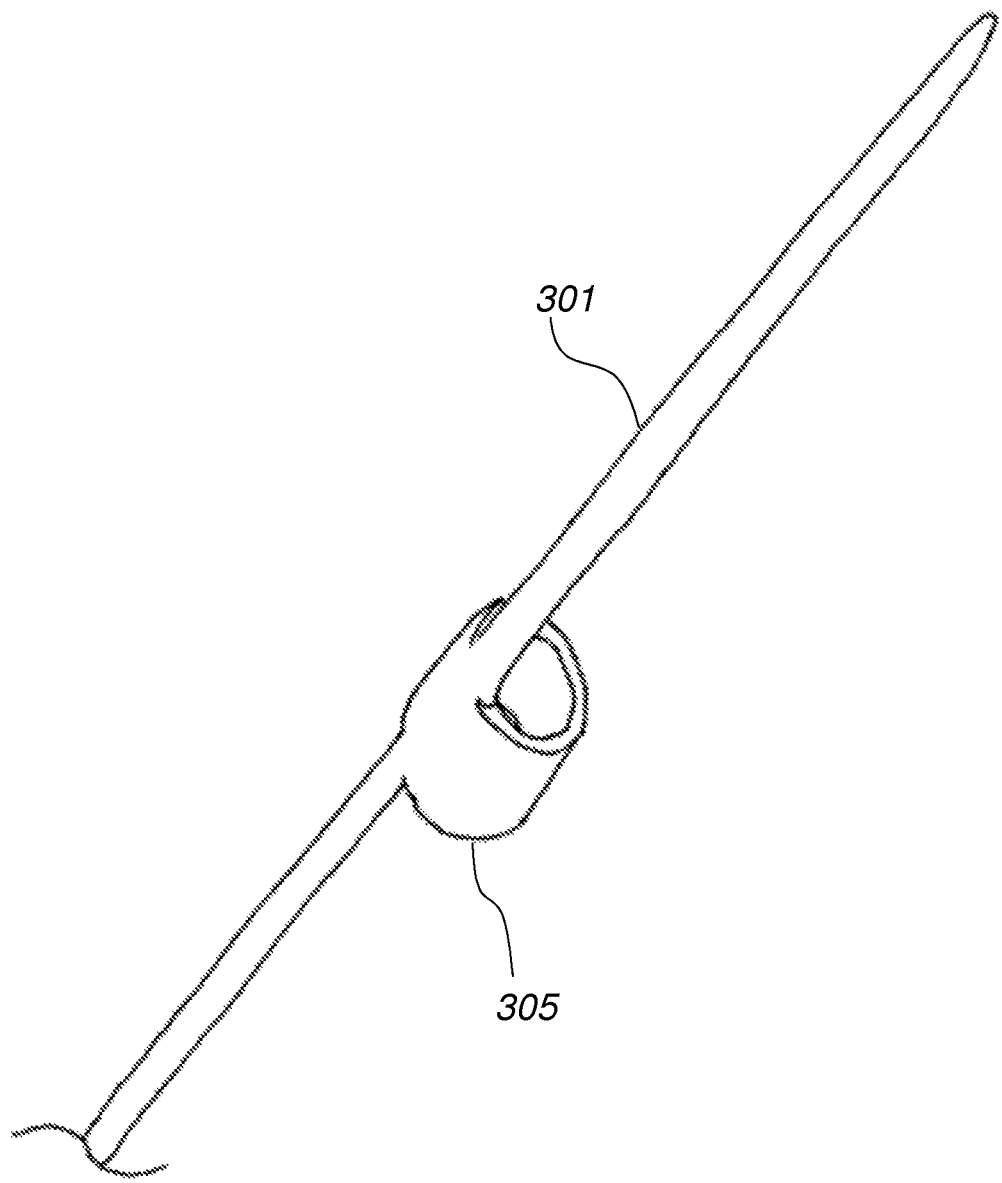
FIG. 3 shows an auxiliary guidewire of the invention.

FIG. 3 shows a distal portion of an auxiliary guidewire 301. Auxiliary guidewire 301 may have any suitable cross-sectional shape such as, for example, round, flat, oval, or kidney shaped in cross-section. Auxiliary guidewire may include one or more of a sleeve 305 dimensioned to be slid over guidewire 201. Sleeve member 305 may include an electroactive polymer. Auxiliary guidewire 301 is preferably a sub-0.014" guidewire and may be slid onto a standard guidewire 201 at the proximal end through the use of one or more sleeve member 305.

Figure 4:
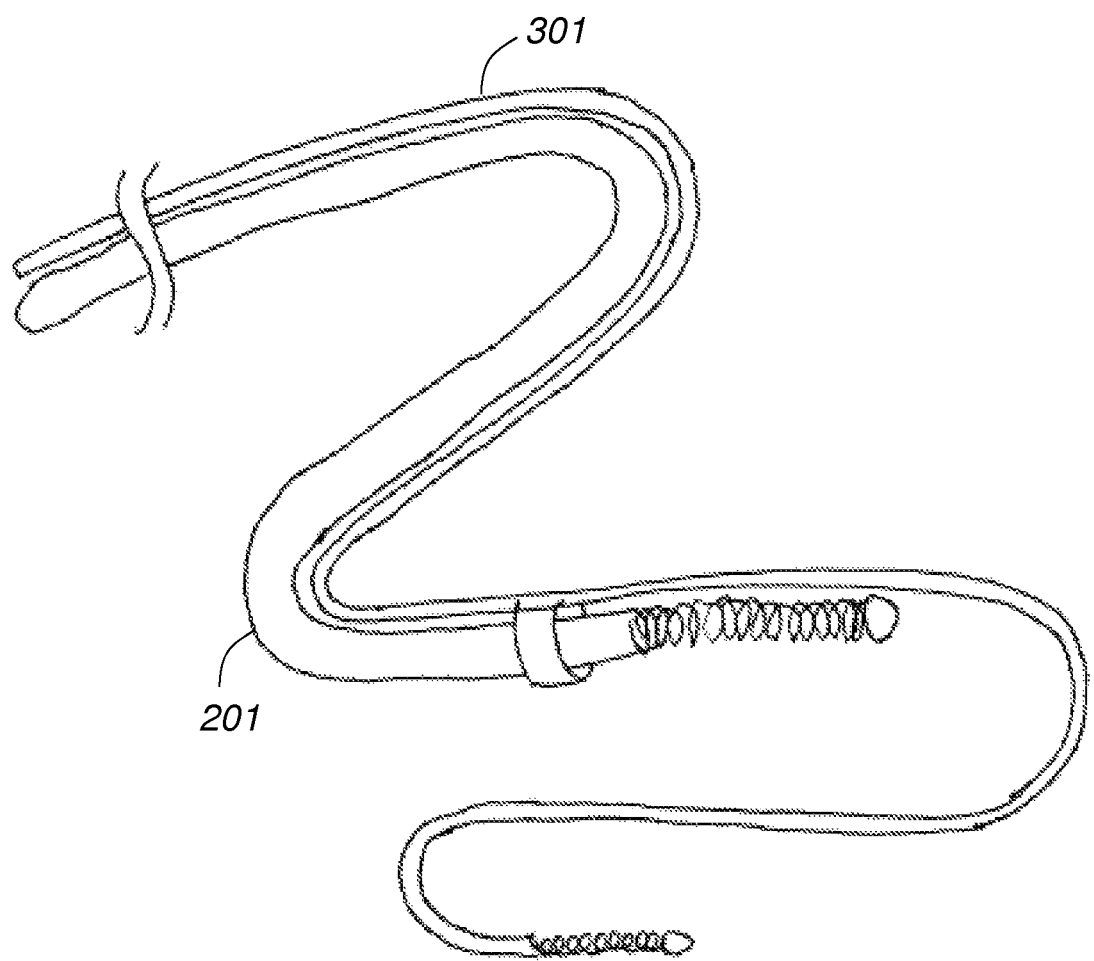
FIG. 4 illustrates a system including an auxiliary guidewire.

FIG. 4 shows an auxiliary guidewire 301 mated to a guidewire 201.

Figure 5:
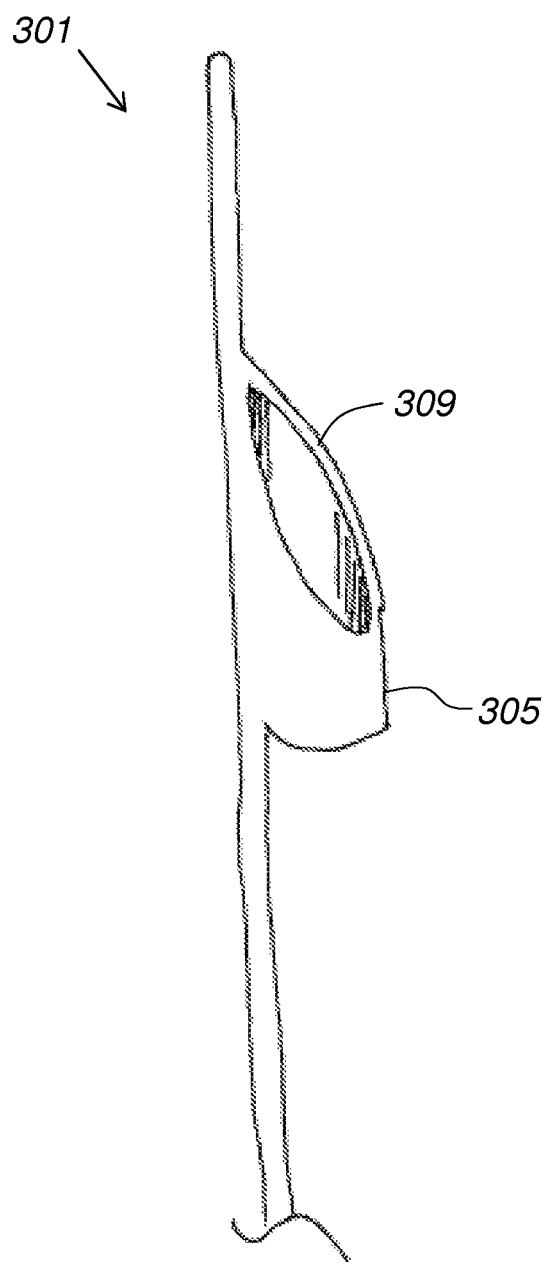
FIG. 5 shows a skive on a sleeve of the auxiliary guidewire.

FIG. 5 depicts an alternative embodiment in which sleeve member 305 includes a skive 309. The inclusion of skive 309 may be beneficial to provide a slope for navigating into fine vasculature. Additionally, the inclusion of skive 309 may be beneficial by increasing an area of aperture into sleeve 305 making it easier to accomplish mating auxiliary guidewire 301 to guidewire 201.

Figure 6:
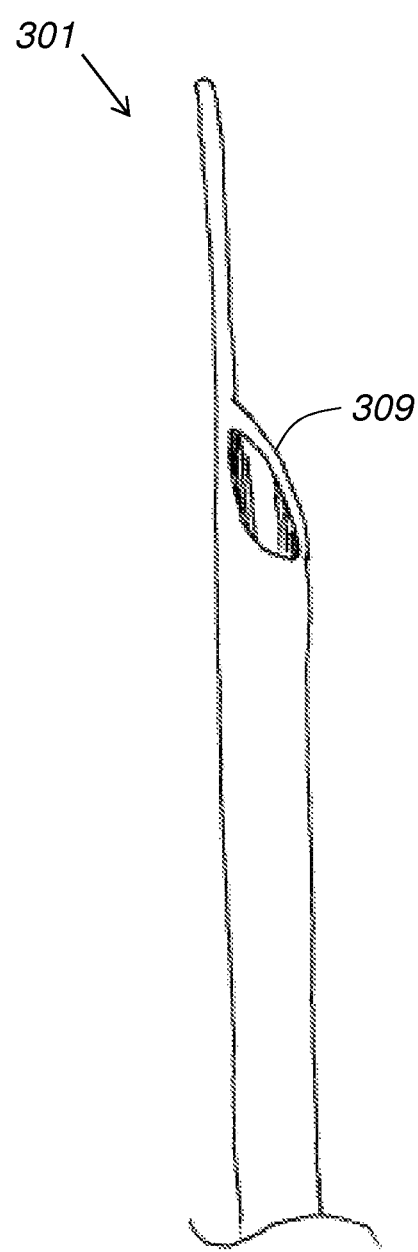
FIG. 6 presents a skive on an auxiliary guidewire.

FIG. 6 depicts an embodiment in which auxiliary guidewire 301 bears an extended lumen terminating at skive 309. This embodiment may be preferred where it is desired to keep auxiliary guidewire 301 substantially against guidewire 201.

In certain embodiments, auxiliary guidewire 301 includes at least one section of electroactive polymer. In some embodiments, sleeve member 305 includes at least one section of electroactive polymer. The electroactive polymer can cause sleeve 305 to deform (e.g., contract or expand) when energized. Sleeve member 305 can thus be expanded allowing insertion and sliding onto guidewire 201. Sleeve member 305 can be retracted or restricted to fix auxiliary guidewire 301 onto guidewire 201. Additionally, the electroactive polymer can be retracted or restricted to shrink sleeve member 305 after removing guidewire 201. Shrinking sleeve member 305 allows passage of a catheter 101 over auxiliary guidewire 201.

Electroactive polymers deform in the presence of an applied electric field, much like piezoelectric actuators. EAPs produce force, strain, deflections, or combination thereof. In general, types of EAPs include ionic, dielectric, and composites. The ionic EAPs operate through the movement of ions within a polymer. The ionic EAPs have the potential of matching the force and energy density of biological muscles. Ionomeric polymer-metal composites (IPMC) are electroactive polymers that bend in response to an electrical activation as a result of the mobility of cations in the polymer network. Generally, two types of base polymers are employed to form IPMCs such as perfluorosulphonate sold under the trademark NAFION by Du Pont and perfluorocaboxylate sold under the trademark FLEMION by Asahi Glass, Japan. IPMC require relatively low voltages to stimulate a bending response (1-10 V) with low frequencies below 1 Hz.

Certain crystals (e.g. quartz, tourmaline and Rochelle salt), when compressed along certain axes, produced a voltage on the surface of the crystal. The reverse effect is also exhibited, whereby application of an electric current deforms the crystal. Any suitable electroactive material may be included. Suitable materials include poly(vinylidene fluoride) or PVDF and its copolymers. These materials include a partially crystalline component in an inactive amorphous phase. Applied AC fields (~200 MV/m) induce electrostrictive (non-linear) strains of about 2%. P(VDF-TrFE) is a PVDF polymer that has been subject to electron radiation and has shown electrostrictive strain as high as 5% at lower frequency drive fields (150 V/mm).

Electrostatic fields can be employed to those polymers exhibiting low elastic stiffness and high dielectric constants to induce large actuation strain, these polymers are known as electro-statically stricted polymers (ESSP) actuators.

Ferroelectric electroactive polymer actuators can be operated in air, vacuum or water and throughout a wide temperature range.

Dielectric electroactive polymers are essentially an elastomeric capacitor. Electrostatic forces cause charged electrodes to compress an intermediate polymer layer, causing a strain response such as an expansion in a direction orthogonal to the compression. The process is also reversible, which can be used to generate electricity or be used as a sensor (much like piezoelectrics). Dielectric electroactive polymers form the basis of the electroactive polymer artificial muscle (EPAM) "spring roll" actuators. Dielectric electroactive polymer actuators can use large electric fields (~100 V/mm) and can produce strain levels (10-200%). An acrylic elastomer tape such as the tape sold under the trademark VHB by 3M is capable of planar strains of more than 300% for biaxially symmetric constraints and linear strains up to 215% for uniaxial constraints.

Electrostrictive graft elastomers include two components, a flexible macromolecule backbone and a grafted polymer that can be produced in a crystalline form. The material exhibits high electric field induced strain (~4%) combined with mechanical power and excellent processability. In some embodiments, the invention provides an electrostrictive-grafted elastomer with a piezoelectric poly(vinylidene fluoride-trifluoro-ethylene) copolymer. This combination has the ability to produce a varied amount of ferroelectric-electrostrictive molecular composite systems. These may be operated as a piezoelectric sensor or even an electrostrictive actuator.

Embodiments of the invention can include electro-viscoelastic elastomers that comprise a silicone elastomer and a polar phase. Upon curing, an electric field is applied that orientates the polar phase within the elastomeric matrix. An applied electric field (<6 V/mm) induces changes in shear modulus.

Liquid crystal elastomer (LCE) materials possess electroactive polymer characteristics by inducing Joule heating. LCEs are composite materials consisting of monodomain nematic liquid crystal elastomers and conductive polymers, which are distributed within their network structure. The actuation mechanism is a phase transition between nematic and isotropic phases. The actuation takes place in less than a second.

Conductive polymers (CP) includes EAPs that actuate via the reversible counter-ion insertion and expulsion that occurs during redox cycling. Significant volume changes occur through oxidation and reduction reactions at corresponding electrodes through exchanges of ions with an electrolyte. Conducive polymer actuators requires voltages in the range of 1-5 V. Variations to the voltage can control actuation speeds. Relatively high mechanical energy densities of over 20 $J/cm^3$ are attained with these materials. Electrodes for conductive polymers may be fabricated from polypyrrole or polyaniline, or PAN doped with HCl. Other material combinations for conductive polymers are polypyrrole, polyethylenedioxythiophene, poly(p-phenylene vinylene)s, polyaniline and polythiophenes.

Carbon Nanotubes (CNT) are polymers that can be actuated via an electrolyte medium and the change in bond length via the injection of charges that affect the ionic charge balance between the nano-tube and the electrolyte. The more charges that are injected into the CNT the larger the dimension change. Due to the mechanical strength and modulus of single CNTs and the achievable actuator displacements, these electroactive polymers can boast the highest work per cycle and generate much higher mechanical stresses than other forms of electroactive polymers.

The inclusion of the electroactive polymer can be used to influence one or more other properties of auxiliary guidewire 301. Any property associated with a dimensional change in response to an applied potential may be included. Exemplary properties include variable stiffness due to the inclusion of at least one section of electroactive polymer at one or more different locations on auxiliary guidewire 301.

In certain embodiments, actuation of the electroactive polymer causes the region surrounding the electroactive polymer section to increase in stiffness, thereby increasing the pushability of auxiliary guidewire 301. Alternatively, actuation of the at least one section of electroactive polymer causes the region surrounding the electroactive polymer section to decrease in stiffness, thereby increasing flexibility of auxiliary guidewire 301.

In one embodiment, the at least one section of electroactive polymer forms part of either the inner or outer shaft of auxiliary guidewire 301. In one embodiment, the at least one section of electroactive polymer is a longitudinal strip. In one embodiment, a shaft of auxiliary guidewire 301 is manufactured of electroactive polymer. In one embodiment, the at least one section of electroactive polymer forms the outer surface of the inner shaft. In one embodiment, the at least one section of electroactive polymer is located in a tip of auxiliary guidewire 301.

An electroactive polymer can provide an ability to curve or turn, for example, to navigate the vasculature system due to strategic positioning of at least one section of electroactive polymer at different locations on the guidewire. In one embodiment, at least one section of electroactive polymer is located only on one side of the inner shaft to control the deflection of the distal tip. In one embodiment, at least one section of electroactive polymer changes the spatial configuration of the guidewire to improve steering around corners. In one embodiment, the guidewire has at least one section of electroactive polymer. In one embodiment, the guidewire tip has at least one section of electroactive polymer. In one embodiment, the at least one section of electroactive polymer in an actuated state causes the guidewire to contract axially. Motions that can be exhibited by auxiliary guidewire 301 include stretching or compression, axial rotation (e.g., torque), lateral vibration, reciprocation (e.g., sawing or toothbrush motion), or any others, or a combination thereof.

In addition to improved navigation through the inclusion of electroactive polymer, auxiliary guidewire 301 exhibits improved navigation by virtue of its small diameter. For example, auxiliary guidewire 301 may be inserted into a vessel into which guidewire 201 will not fit.

Figure 7:
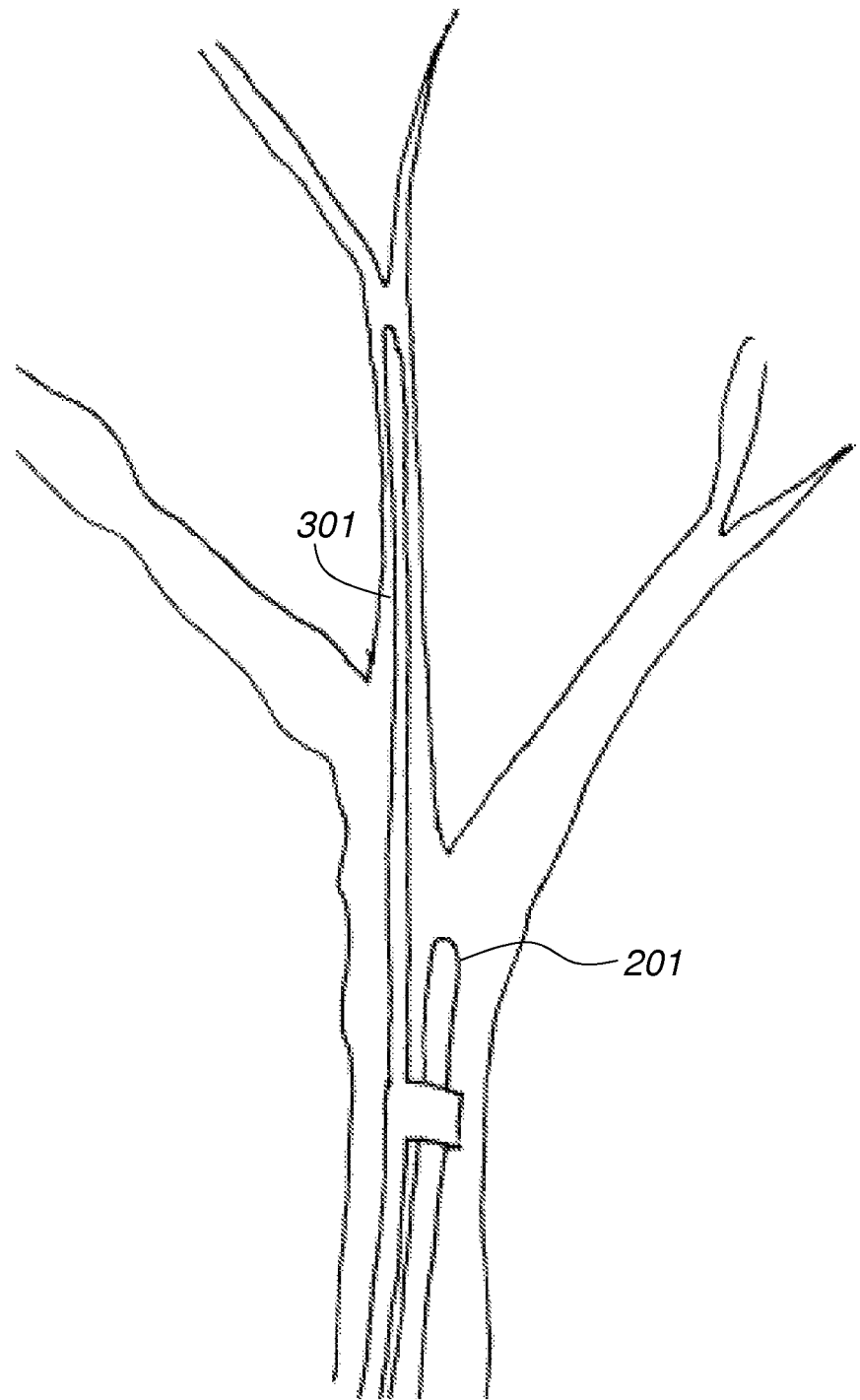
FIG. 7 depicts use of an auxiliary guidewire to access fine vasculature.

FIG. 7 illustrates a navigational advantage provided by auxiliary guidewire 301. Inserting guidewire 201 provides a path for auxiliary guidewire 301 to follow. Auxiliary guidewire 301 provides a means for navigating further down the vasculature than is possible with only guidewire 201.

The fine vasculature navigability of auxiliary guidewire 301 in combination with the improved dexterity of auxiliary guidewire 301 provide further navigational advantages. For example, due to the inclusion of at least one electroactive polymer, auxiliary guidewire 301 by be turned to enter an off-axis branch.

Further, auxiliary guidewire 301 may bifurcate from guidewire 201 at a point proximal from a distal tip of guidewire 201 (e.g., auxiliary guidewire 301 and guidewire 201 form a "Y" shape). As a result, a physician can navigate into both branches of a bifurcation in a vessel.

Figure 8:
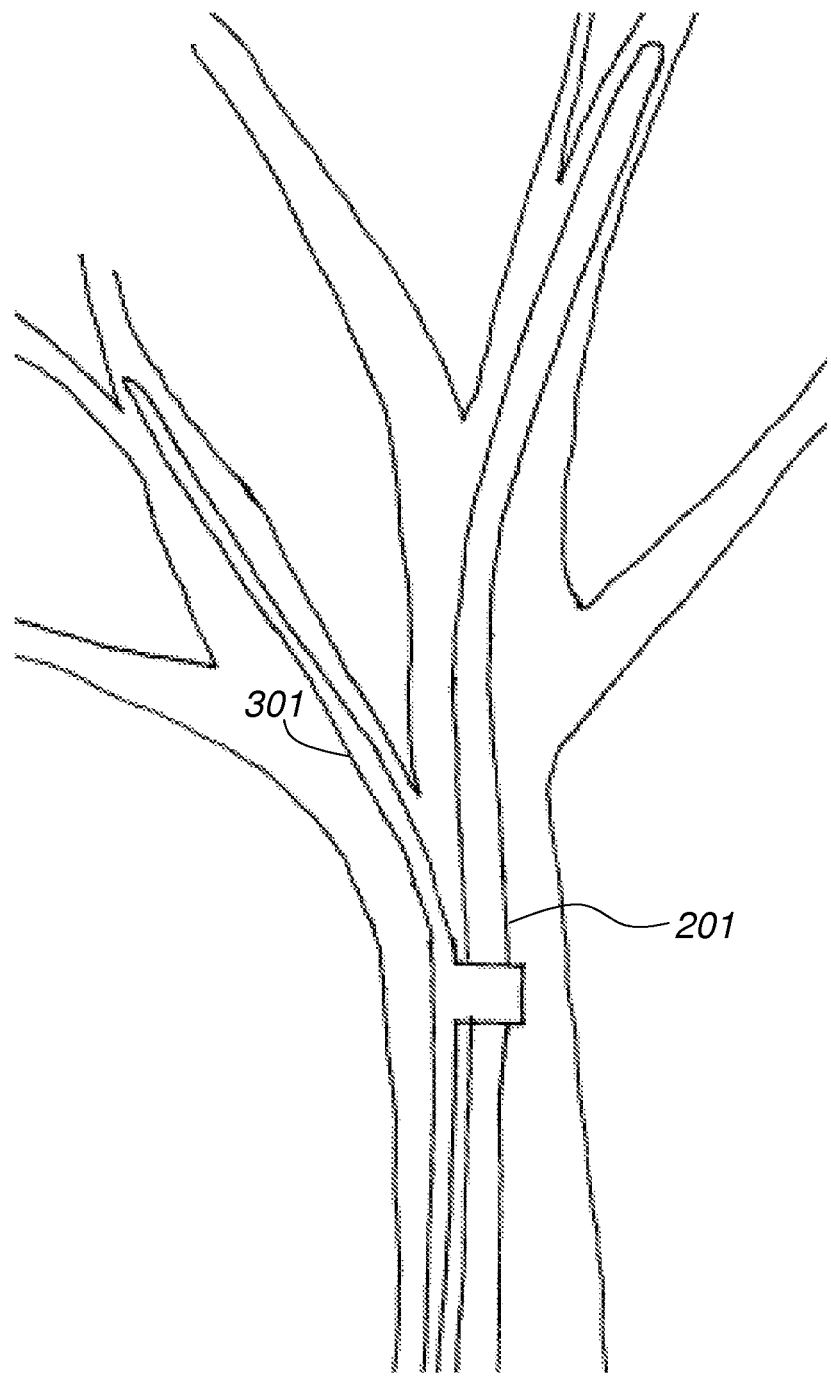
FIG. 8 shows use of a system of the invention to choose a branch of a bifurcation.

FIG. 8 illustrates use of auxiliary guidewire 301 to navigate into paths that branch off from the vasculature tracked by guidewire 201. Navigating a bifurcation is known in the art to be a difficult challenge. See, e.g., Suzuki, et al., 2013, A novel guidewire approach for handling acute-angle bifurcations, J Inv Cardiol 25(1):48-54; Lefevre, et al., 2007, Stenting of bifurcation lesions, J Interven Cardiol 14(6):573-585; and Oesterle, et al., 2005, Angioplasty at coronary bifurcations, Cath Card Diag 12(1):57-63, the contents of each of which are incorporated by reference.

Where a bifurcated vessel must be treated, the bifurcation shown in FIG. 8 may be obtained. The physician may then view the disposition of auxiliary guidewire 301 and guidewire 201 (e.g., via angiography) and determine which branch of the bifurcation to send the treatment catheter to. Whichever branch the physician determines to treat, the guidewire corresponding to the other branch can then be removed. Thus an auxiliary guidewire 301 gives the ability to select which branch of a bifurcated vessel to send a catheter to. Bifurcation is discussed in U.S. Pat. No. 8,088, 102 to Adams; U.S. Pat. No. 7,300,460 to Levine; U.S. Pub. 2009/0326634 to Vardi; and U.S. Pub. 2001/0049548 to Vardi, the contents of each of which are incorporated by reference.

Due to the fact that curvature of auxiliary guidewire 301 can be induced from a computer workstation (e.g., by a mouse, joystick, or computer keys), auxiliary guidewire 301 can be navigated through or into vessels, even where tortuous or branched. For example, a physician may refer to an angiographic display. Angiography systems can be used to visualize the blood vessels by injecting a radio-opaque contrast agent into the blood vessel and imaging using X-ray based techniques such as fluoroscopy.

Angiographic techniques include projection radiography as well as imaging techniques such as CT angiography and MR angiography. In certain embodiments, angiography involves using an x-ray contrast agent and an x-ray system to visualize the arteries and guidewire 201. X-ray images of the transient radio contrast distribution within the blood flowing within the coronary arteries allows visualization of the location of guidewire 201, particularly in relation to the artery openings.

A physician may refer to the angiography display to navigate guidewire 201. Angiography systems and methods are discussed, for example, in U.S. Pat. Nos. 7,734,009; 7,564,949; 6,520,677; 5,848,121; 5,346,689; 5,266,302; 4,432,370; and U.S. Pub. 2011/0301684, the contents of each of which are incorporated by reference in their entirety for all purposes. Useful catheters and guidewires are discussed in U.S. Pat. Nos. 7,766,896 and 7,909,844, the contents of which are incorporated by reference.

Auxiliary guidewire 301 may include a size adjustment mechanism to adjust the circumferential size of the guidewire. In the embodiment, the size adjustment mechanism may operate through a pair of electroactive polymer actuators. The electroactive polymer actuators are configured to undergo deflection upon actuation to adjust the circumferential size of the guidewire.

In general, auxiliary guidewire 301 may include one or more electroactive polymer actuator with an elastomeric polymer positioned between a pair of electrodes. The elastomeric polymer layer may be configured to deflect when a voltage difference is applied across the elastomeric polymer layer. The electroactive polymer actuator can include one or more of any of a number of polymers, including, for example, dielectric electrostrictive electroactive polymers, ion-exchange electroactive polymers, and ionomeric polymer-metal composite electroactive polymers. For certain implementations, dielectric electrostrictive electroactive polymers are particularly desirable because of their response times and operational efficiencies. Specific examples of polymers that can be used include Nusil CF19-2186 (available from Nusil Technology, Carpenteria, Calif.); dielectric elastomeric polymers; silicone rubbers; silicone elastomers; acrylic elastomers, such as VHB 4910 acrylic elastomer (available from 3M Corporation, St. Paul, Minn.); silicones, such as Dow Corning HS3 (available from Dow Corning, Wilmington, Del.); fluorosilicones, such as Dow Corning 730 (available from Dow Corning, Wilmington, Del.); acrylic polymers, such as acrylics in the 4900 VHB acrylic series (available from 3M Corporation, St. Paul, Minn.); polyurethanes; thermoplastic elastomers; copolymers including poly(vinylidene fluoride); pressure-sensitive adhesives; fluoroelastomers; polymers including silicone and acrylics, such as copolymers including silicone and acrylic and polymer blends including a silicone elastomer and an acrylic elastomer; and combinations of two or more of these polymers. Electroactive polymers are discussed in U.S. Pat. Nos. 8,206,429; 8,133,199; 6,514,237; 5,573,520; 4,830,023; U.S. Pub. 2012/0265268; and U.S. Pub. 2007/0208276, the contents of which are incorporated by reference. Use of electroactive polymers is discussed further in U.S. Pat. Nos. 8,100,838; 8,021,377; 6,969,395; 6,139,510; U.S. Pub. 2005/0165439; and U.S. Pub. 2004/0220606, the contents of which are incorporated by reference.

In some embodiments, at least one section of electroactive polymer forms a spiral about auxiliary guidewire 301. The spiral may be, for example, a single, multiple sections of electroactive polymer or one continuous section of electroactive polymer. In at least one embodiment, there are several sections of electroactive polymer which form an overall spiral pattern. In at least one embodiment, the at least one section of electroactive polymer extends substantially the entire length of the guidewire in a spiral pattern. A spiral section of electroactive polymer can be selectively actuated to cause forced curvature or straightening of auxiliary guidewire 301. For example, after auxiliary guidewire 301 is deployed in a vessel and has been used, it may lie in a curved shape which could interfere with, for example, a deployed stent while the guidewire is being withdrawn. In at least one embodiment, selective actuation will resist or prevent the inner shaft from holding, adopting, or maintaining the curvature or shape of a vessel during withdrawal of the guidewire.

As discussed herein, the actuation of the electroactive polymer improves the steering of the guidewire around corners or turns as the guidewire traverses the vasculature.

The auxiliary guidewire 301 can be manufactured by co-extruding a removable nylon wire in the wall of the guidewire shaft. After the nylon wire is pulled out, the resulting shaft can be coated with a conductive ink to form the electrode and filled with an electroactive polymer by electro polymerization. The counter electrode can be a conductive ink on the outside of the guidewire shaft. Each axial section of electroactive polymer may be deposited on one fraction of the circumference of a metallic auxiliary guidewire 301. A counter electrode can be deposited or printed on an insulator, which is positioned on auxiliary guidewire 301 opposite from the section of electroactive polymer. Actuation of the section of electroactive polymer causes auxiliary guidewire 301 to bend in a direction that is opposite from where the section of electroactive polymer coats auxiliary guidewire 301. Desirably, in use, these axial sections of electroactive polymer will allow the physician to control the direction of auxiliary guidewire 301 and allow for better maneuvering within the body lumen.

In at least one embodiment, auxiliary guidewire 301 includes a polymer heat shrink tube made from polyester (PET). A conductive ink, for example, but not limited to, a silver or gold ink from Erconinc can be deposited onto the PET film. Because lines of conductive ink can be made very fine, multiple conductor lines can be printed along auxiliary guidewire 301. At the position of the electroactive polymer actuator, a larger surface can be printed and the electroactive polymer deposited.

Additionally or alternatively, an electroactive polymer can be used to stiffen or un-stiffen (e.g., make floppy) select portions of auxiliary guidewire 301. Auxiliary guidewire 301 may include a plurality of longitudinal strips of electroactive polymer positioned about the circumference of the guidewire shaft. Multiple strips of electroactive polymer, located at the same circumferential coordinate, may be positioned along the longitudinal length of the guidewire shaft. The exact placement about the circumference of the guidewire shaft is not critical so long as the strips of electroactive polymer are located about the entire circumference of the shaft along the area(s) where control of the flexibility/rigidity of the guidewire shaft is desired. Desirably, actuation of the longitudinal strips of electroactive polymer modifies the rigidity of the guidewire shaft in the region of the electroactive polymer strips. The strips may then be used to increase the stiffness and decrease the flexibility of the guidewire. In one embodiment, the longitudinal strips decrease in size when actuated and decrease the stiffness and increase the flexibility of the guidewire. In one embodiment, longitudinal strips of electroactive polymer are positioned about the circumference of the guidewire shaft and extend from the proximal end region of the guidewire shaft to the distal end region of the guidewire shaft. In addition, the number of strips of electroactive polymer positioned about the circumference of the guidewire shaft can vary. The actuator mechanism generally includes electrodes. The electrodes of different sections of electroactive polymer are separate from one another so that precise actuation of the desired section(s) of electroactive polymer can be done. An exterior surface of a strip of electroactive polymer may be substantially flush with the exterior surface of the guidewire shaft. In some embodiments, the strip of electroactive polymer may form only a portion of the wall of the guidewire shaft, i.e. the strip of electroactive polymer does not have the same thickness as the wall of the guidewire shaft and is not flush with either the exterior surface or the interior surface of the shaft.

In certain embodiments, stiff elements, e.g. stiff polymer strips, are engaged to a layer of electroactive polymer. If a guidewire 201 with greater stiffness is desired, the layer of electroactive polymer is actuated. Actuation of the layer of electroactive polymer causes the electroactive polymer to volumetrically increase in size and moves the stiff polymer strips outwards, to cause an increase in the stiffness of the guidewire 201 because the stiffness increases with the fourth power of the size. The polymer strips may extend along the entire length of the guidewire 201 or the strips may be positioned at particular areas along the length of the guidewire 201 where control of the stiffness of the guidewire shaft is desired. Similarly, the layer of electroactive polymer may extend along the entire length of the guidewire 201 or the layer of electroactive polymer may be placed at particular areas along the length of the guidewire 201 where control of the stiffness of the guidewire shaft is desired. In one embodiment, at least one portion of the guidewire has a layer of electroactive polymer with at least one strip of stiff polymer engaged thereto. Examples of suitable materials to be used for the stiff polymer strips include, but are not limited to, polyamides, polyethylene (PE), Marlex high density polyethylene, polyetheretherketone (PEEK), polyamide (PI), and polyetherimide (PEI), liquid crystal polymers (LCP), acetal and any mixtures or combinations thereof. The polymer and actuators may be placed, for example, as described in U.S. Pub. 2005/0165439.

The parts of auxiliary guidewire 301 of the present invention may be manufactured from any suitable material to impart the desired characteristics and electroactive polymers. Examples of suitable materials include, but are not limited to, polymers such as polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro(propyl vinyl ether) (PFA), polyether-ester, polymer/metal composites, etc., or mixtures, blends or combinations thereof. One example of a polyether block ester is available under the trade name ARNITEL, and one suitable example of a polyether block amide (PEBA) is available under the trade name PEBA, from ATOMCHEM POLYMERS, Birdsboro, Pa.

The guidewires of the present invention are actuated, at least in part, using electroactive polymer actuators. Electroactive polymers are characterized by their ability to change shape in response to electrical stimulation. Electroactive polymers include electric electroactive polymers and ionic electroactive polymers. Piezoelectric materials may also be employed. Electric electroactive polymers include ferroelectric polymers, dielectric electroactive polymers, electrorestrictive polymers such as the electrorestrictive graft elastomers and electroviscoelastic elastomers, and liquid crystal elastomer materials.

Additional information regarding electroactive polymer actuators, their design considerations, and the materials and components that may be employed therein, can be found, for example, in U.S. Pat. Nos. 7,777,399; 6,258,052; 6,249,076; 6,139,510; 5,693,015; 5,120,308; U.S. Pub. 2006/0100694; and U.S. Pub. 2006/0074442 each of which is hereby incorporated by reference in its entirety. Furthermore, networks of conductive polymers may also be employed. For example, it has been known to polymerize pyrrole in electroactive polymer networks such as poly(vinylchloride), poly(vinyl alcohol), a perfluorinated polymer that contains small proportions of sulfonic or carboxylic ionic functional groups, available from E.I. DuPont Co., Inc. (Wilmington, Del.). Electroactive polymers are also discussed in U.S. Pub. 2004/0143160 and U.S. Pub. 2004/0068161, the contents of each of which are incorporated by reference.

As used herein, the word "or" means "and or or", sometimes seen or referred to as "and/or", unless indicated otherwise.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of inserting a catheter into a selected branch of a bifurcation, the method comprising:
    viewing the bifurcation on an angiographic display;
    identifying a select branch of the bifurcation for treatment;
    inserting a guidewire up to the bifurcation, wherein the bifurcation comprises a first diameter, and wherein the branch comprises a smaller second diameter;
    sliding a sleeve member of an auxiliary guidewire over the guidewire such that a distal portion of the auxiliary guidewire is moved to the select branch, wherein the sleeve member comprises an annular body, and wherein the auxiliary guidewire, and not the guidewire, is configured to be inserted into the select branch;
    sending the auxiliary guidewire down the select branch and the guidewire down a different branch;
    identifying which of the auxiliary guidewire and the guidewire is within the select branch by the angiographic display;
    removing the other of the auxiliary guidewire and the guidewire; and
    delivering a catheter to the select branch.

2. A method, comprising:
    inserting a first guidewire into a vessel comprising a bifurcation into a first branch and a second branch smaller than the first branch, wherein the vessel comprises a first diameter at the bifurcation, and wherein the second branch comprises a smaller second diameter;
    moving the first guidewire through the vessel to the bifurcation;
    inserting a second guidewire into the vessel along the first guidewire, wherein the second guidewire comprises an extended body and a sleeve member, wherein the sleeve member comprises an annular body, wherein a distal portion of the extended body projects from a distal surface of the annular body, wherein the inserting a second guidewire into the vessel includes moving the sleeve member over the first guidewire, wherein the extended body of the second guidewire comprises a smaller diameter than the first guidewire, and wherein the extended body of the second guidewire, and not the first guidewire, is configured to be inserted into the second branch;

moving the first guidewire into the first branch;

moving the extended body of the second guidewire into the second branch based on the smaller diameter of the extended body;

selecting the first branch or the second branch to treat;

when the first branch is selected,
  removing the second guidewire from the second branch; and
  inserting a treatment catheter into the first branch along the first guidewire; and when the second branch is selected,
  removing the first guidewire from the first branch; and
  inserting the treatment catheter into the second branch along the second guidewire.

3. The method of claim 2, wherein the inserting the second guidewire into the vessel along the first guidewire includes:
  positioning the first guidewire through the sleeve member of the second guidewire.

4. The method of claim 3, wherein the sleeve member comprises an electroactive polymer, the method further comprising:
  activating the electroactive polymer to deform the sleeve member.

5. The method of claim 4, wherein the activating the electroactive polymer to deform the sleeve member includes at least one of:
  expanding the sleeve member such that the first guidewire is positionable within the sleeve member; or
  contracting the sleeve member such that the first guidewire is coupled to the second guidewire.

6. The method of claim 4, wherein the activating the electroactive polymer to deform the sleeve member includes:
  contracting the sleeve member to allow the inserting the treatment catheter into the second branch along the second guidewire.

7. The method of claim 2, wherein the second guidewire comprises an electroactive polymer, the method further comprising:
  activating the electroactive polymer.

8. The method of claim 7, wherein the activating the electroactive polymer includes:
  increasing stiffness of the second guidewire.

9. The method of claim 7, wherein the activating the electroactive polymer includes:
  deflecting a distal tip of the second guidewire.

10. The method of claim 7, wherein the activating the electroactive polymer includes:
  moving the second guidewire to enter the second branch that is off-axis from the first branch.

11. The method of claim 2, wherein the selecting the first branch or the second branch to treat includes:
  visualizing, using angiography, the first guidewire within the first branch and the second guidewire within the second branch.

12. The method of claim 2, wherein the first guidewire comprises a 0.014 inch diameter guidewire and the second guidewire comprises a sub-0.014 inch diameter guidewire.

13. The method of claim 2, wherein the sleeve member completely surrounds the first guidewire.

14. The method of claim 2, wherein the distal surface of the annular body is in a plane orthogonal or oblique to a longitudinal axis of the second guidewire.

15. The method of claim 2, wherein the sleeve member is integral with the extended body such that the distal portion of the extended body forms a portion of a perimeter of the extended body.

16. The method of claim 15, wherein the annular body comprises a first thickness, and wherein the distal portion of the extended body comprises a second thickness that is less than or equal to the first thickness.

17. The method of claim 1, wherein the distal portion of the auxiliary guidewire projects from a distal surface of the annular body.

18. The method of claim 15, wherein the perimeter of the sleeve member defines a longitudinal opening through which the first guidewire extends.

19. The method of claim 17 wherein the distal surface of the annular body is in a plane orthogonal or oblique to a longitudinal axis of the auxiliary guidewire.

20. The method of claim 18, wherein the longitudinal opening is laterally offset from an axis of the second guidewire.

* * * * *